US012673935B2

(12) United States Patent
Yu et al.

(10) Patent No.: US 12,673,935 B2
(45) Date of Patent: Jul. 7, 2026

(54) PYRIMIDINE DERIVATIVE, AND PREPARATION METHOD THEREFOR AND USE THEREOF

(71) Applicant: CGENETECH (SUZHOU, CHINA) CO., LTD., Suzhou (CN)

(72) Inventors: Qiang Yu, Suzhou (CN); Juping Ding, Suzhou (CN); Mulin Tang, Suzhou (CN); Yan Hao, Suzhou (CN); Qin Lu, Suzhou (CN); Shen Qian, Suzhou (CN); Xusheng Tian, Suzhou (CN)

(73) Assignee: CGENETECH (SUZHOU, CHINA) CO., LTD., Suzhou (CN)

( * ) Notice: Subject to any disclaimer, the term of this patent is extended or adjusted under 35 U.S.C. 154(b) by 742 days.

(21) Appl. No.: 18/145,601

(22) Filed: Dec. 22, 2022

(65) Prior Publication Data

US 2023/0125233 A1 Apr. 27, 2023

Related U.S. Application Data

(63) Continuation of application No. PCT/CN2021/104379, filed on Jul. 2, 2021.

(30) Foreign Application Priority Data

Jul. 3, 2020 (CN) ........................ 202010629992.X

(51) Int. Cl.
*C07D 401/14* (2006.01)

(52) U.S. Cl.
CPC .................................. *C07D 401/14* (2013.01)

(58) Field of Classification Search
CPC .................................................. C07D 401/14
See application file for complete search history.

(56) References Cited

U.S. PATENT DOCUMENTS

2020/0339572 A1 10/2020 Wu et al.

FOREIGN PATENT DOCUMENTS

| | | | |
|---|---|---|---|
| CN | 102264725 A | 11/2011 | |
| CN | 105294655 A | 2/2016 | |
| CN | 107793399 A | 3/2018 | |
| CN | 108794452 A | 11/2018 | |
| CN | 109310684 A | 2/2019 | |
| EP | 3620456 A1 | 3/2020 | |
| JP | 2019511526 A | 4/2019 | |
| KR | 20180129918 A | 12/2018 | |
| WO | WO-2016015605 A1 * | 2/2016 | ............... A61P 9/10 |
| WO | 2018045957 A1 | 3/2018 | |
| WO | 2020108661 A1 | 6/2020 | |

OTHER PUBLICATIONS

International Search Report issued in International Application No. PCT/CN2021/104379, mailed Sep. 27, 2021,10 pgs.
First Office Action issued in Chinese Application No. 202010629992.X, mailed Mar. 9, 2022; 17 pgs.
Extended Search Report in European Application No. 21834581.7, dated May 31, 2024; 12 pgs.
Notice of Reasons for Refusal in Corresponding Japanese Application No. 2022-579075, mailed Jan. 23, 2024; 7 pgs.
First Office Action in Corresponding Korean Application No. 1054-200077, dated Feb. 13, 2025; 12 pgs.

* cited by examiner

*Primary Examiner* — John S Kenyon
*Assistant Examiner* — Rehana Ismail
(74) *Attorney, Agent, or Firm* — HAUPTMAN HAM, LLP

(57) ABSTRACT

Provided is a pyrimidine derivative, a preparation method and a use thereof, wherein the pyrimidine derivative is selected from a compound represented by Formula (I), or a tautomer, an enantiomer, a diastereomer, a mesomer, a racemate, or a mixture thereof, or a pharmaceutically acceptable salt or prodrug thereof. The pyrimidine derivative shows an excellent CDK-inhibiting effect and action.

Formula (I)

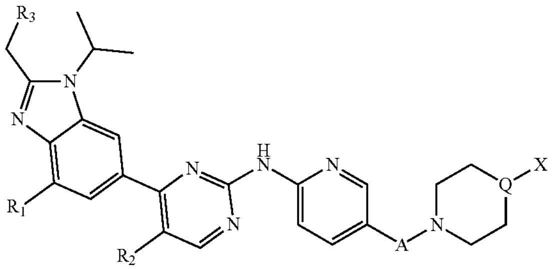

6 Claims, No Drawings

PYRIMIDINE DERIVATIVE, AND PREPARATION METHOD THEREFOR AND USE THEREOF

CROSS-REFERENCE TO RELATED APPLICATIONS

The present invention is a Continuation of International Application No. PCT/CN2021/104379, filed Jul. 2, 2021, which claims priority to Chinese patent application No. 202010629992.X filed with the China National Intellectual Property Administration on Jul. 3, 2020, and entitled "Pyrimidine derivative and preparation method and use thereof", both of which are hereby incorporated by reference herein in their entireties.

TECHNICAL FIELD

The invention relates to a compound, and in particular, to a pyrimidine derivative and a preparation method and a use thereof.

BACKGROUND

A large number of studies have found that tumors are related to abnormal cell cycle, and most of tumor cells involve three basic cell cycle defects—an enormous number of mitotic signaling protein mutations/anti-mitotic signaling protein defects, as well as genome instability (GIN) and chromosomal instability (CIN), which are all directly or indirectly caused by the deregulation of cyclin-dependent kinase (CDK). CDK works by binding to its regulatory subunit cyclins, while four large classes of cyclins (A-, B-, D-, and E-cyclins) play different roles in different stages of the whole cell cycle. At least 16 mammalian cyclins have been identified. Cyclin B/CDK1, Cyclin A/CDK2, Cyclin E/CDK2, Cyclin D/CDK4, Cyclin D/CDK6, Cyclin T1/CDK9 and other heterodimers (including CDK3 and CDK7) are important regulators for cell cycle progress. Other functions of Cyclin/CDK heterodimers include the regulation of transcription, DNA repair, differentiation, and programmed cell death. (Morgan D O. Cyclin-dependent kinases: engines, clocks, and microprocessors. Annu. Rev. Cell. Dev. Biol. (1997) 13:261-291).

Studies have shown that increased activity or abnormal activation of cyclin-dependent kinase may lead to the formation of human tumor. In fact, the formation of human tumor is generally related to the changes of CDK protein itself or its regulators. Studies have found that CDK4 and CDK6 are highly homologous, CDK4 single-gene knockout mice have diabetes symptoms and cell defects, CDK6 single-gene knockout mice have slight anemia symptoms caused by hematopoietic cell proliferation defects, while CDK4 and CDK6 (CDK4/6) double-gene knockout may have impaired proliferative capability of hematopoietic precursor cells, resulting in late embryonic death of double-gene knockout mice. Overactivation of CDK4/6-Cyclin D/Rb (phosphorylated retinoblastoma gene) signaling pathway is commonly found in tumor cells. Stimulated by various mitotic signals inside and outside the cell, Cyclin D is highly expressed, the interaction between CDK4/6 protein and Cyclin D is regulated, thus promoting the localization and kinase activity of CDK4/6. Activated CDK4/6 allows the dissociation of Rb-E2F complex by phosphorylating Rb, to release free E2F into the nucleus, thereby regulating protein transcription and starting the cell cycle. Overactivation of CDK4 often occurs in epithelial malignant tumors, while overactivation of CDK6 often occurs in interstitial cell tumors, such as sarcoma and hematological cancer. As found in the constructed mouse model with breast cancer, wild-type nude mice were all subject to tumor formation, but no tumor was formed in CDK4 knockout nude mice at all; while the tumor growth in nude mice was found to be significantly inhibited by interference of the expression of CDK4 with anti-CDK4 siRNA.

As found in in-vitro experiments, naturally occurring protein inhibitors for CDK, such as p16 and p27, can inhibit the growth of lung cancer cell line. Studies have also found that cyclin E (CDK2-regulated cyclin) is commonly over-expressed in cancer. For a long time, amplification or overexpression of cyclin E is related to the poor prognosis of breast cancer. (Keyomarsi et al., Cyclin E and survival in patients with breast cancer. N Engl J Med. (2002) 347: 1566-75). Cyclin E2 (CCNE2) overexpression is associated with endocrine resistance in breast cancer cells, it has been reported that CDK2 inhibition can restore sensitivity to tamoxifen or CDK4 inhibitor in tamoxifen resistant and CCNE2 overexpressing cells. (Caldon et al., Cyclin E2 overexpression is associated with endocrine resistance but not insensitivity to CDK2 inhibition in human breast cancer cells. Mol Cancer Ther. (2012) 11:1488-99; Herrera-Abreu et al., Early Adaptation and Acquired Resistance to CDK4/6 Inhibition in Estrogen Receptor-Positive Breast Cancer, Cancer Res. (2016) 76: 2301-13). Cyclin E amplification has been reported to contribute to trastuzumab resistance in HER2+ breast cancer as well. (Scaltriti et al., Cyclin E amplification/overexpression is a mechanism of trastuzumab resistance in HER2+ breast cancer patients, Proc Natl Acad Sci. (2011) 108: 3761-3766). Cyclin E overexpression has also been reported to play a role in basal-like and triple negative breast cancer (TNBC) and inflammatory breast cancer. (Elsawaf & Sinn, Triple Negative Breast Cancer: Clinical and Histological Correlations, Breast Care (2011) 6:273-278 Alexander et al., Cyclin E overexpression as a biomarker for combination treatment strategies in inflammatory breast cancer, Oncotarget (2017) 8: 14897-14911). Amplification or overexpression of Cyclin E1 (CCNE1) is also related to poor prognosis in ovarian cancer, gastric cancer, endometrial cancer, and other cancers. (Nakayama et al., Gene amplification CCNE1 is related to poor survival and potential therapeutic target in ovarian cancer, Cancer (2010) 116: 2621-34; Etemadmoghadam et al., Resistance to CDK2 Inhibitors Is Associated with Selection of Polyploid Cells in CCNE1-Amplified Ovarian Cancer, Clin Cancer Res (2013) 19: 5960-71; Au-Yeung et al., Selective Targeting of Cyclin E1-Amplified High-Grade Serous Ovarian Cancer by Cyclin-Dependent Kinase 2 and AKT Inhibition, Clin. Cancer Res. (2017) 23:1862-1874; Ayhan et al., CCNE1 copynumber gain and overexpression identify ovarian clear cell carcinoma with a poor prognosis, Modern Pathology (2017) 30: 297-303; Ooi et al., Gene amplification of CCNE1, CCND1, and CDK6 in gastric cancers detected by multiplex ligation-dependent probe amplification and fluorescence in situ hybridization, Hum Pathol. (2017) 61: 58-67; Noske et al., Detection of CCNE1/URI (19q12) amplification by in situ hybridisation is common in high grade and type II endometrial cancer, Oncotarget (2017) 8: 14794-14805). Dinaciclib (MK-7965), a small molecule inhibitor for inhibiting CDK1, CDK2, CDK5 and CDK9, is currently undergoing clinical development against breast cancer and blood cancer. A treatment of advanced solid tumors by combination of Seliciclib (roscovitine or CYC202) inhibiting CDK2, CDK 7 and CDK 9 with chemotherapy is also in research.

Besides inhibiting tumor growth, CDK inhibitors can also be used for: treating cardiovascular disorders, such as restenosis, atherosclerosis, and other vascular disorders caused by abnormal cell proliferation; treating diseases caused by various infectious agents, including fungi, protozoan parasites (such as *Plasmodium falciparum*) and DNA and RNA viruses; and ameliorating various autoimmune disorders. Studies have found that in the rat model of arthritis, joint swelling is basically inhibited by p16-expressing adenovirus virus treatment, and CDK inhibitors show an effective resistance to other cell proliferation disorders, including psoriasis (characterized by excessive proliferation of keratinocytes), glomerulonephritis, and lupus.

Studies have also found that cells in GUS and G2/M phases in a cell cycle are extremely sensitive to DNA damaging agents such as ionizing radiation (IR), and the process of cell transition from G1 phase to S phase at least needs to be regulated through co-phosphorylation of Rb family proteins by three cyclin-dependent kinases (CDK2, CDK4 and CDK6) and their regulatory subunit cyclins. Selective CDK4/6 inhibitor can induce G1 phase retardation of cells, thus improving the tolerance of hematopoietic stem/progenitor cells to DNA damaging agents such as IR, and effectively reducing various hematopoietic toxicities caused by radiation, including myelosuppression, neutropenia, leukopenia, anemia, etc.

Studies have also found that CDK2 overexpression is related to the abnormal regulation of cell cycle. A cyclin E/CDK2 complex plays an important role in regulating GUS conversion, histone biosynthesis, and centrosome replication. The progressive phosphorylation of Rb by cyclin D/CDK4/6 and cyclin E/CDK2 allows releasing G1 transcription factor E2F and promoting the entry of S phase. Cyclin A/CDK2 activation during the early S phase promotes phosphorylation of endogenous substrates, which allows DNA replication and inactivation of E2F to complete the S phase. (Asghar et al., The history and future of targeting cyclin-dependent kinasesin cancer therapy, Nat. Rev. Drug. Discov. 2015; 14(2): 130-146).

The disclosed patent applications of inhibitors selectively inhibiting CDK4 and CDK6 include WO2003062236, WO2006008874, WO2009126584, etc. Despite great efforts, no drugs targeting CDK2 have been approved so far, and CDK inhibitors with new activity spectrum, especially those targeting CDK2, still need to be discovered.

The information disclosed in the Background section is only intended to enhance understanding of the general background of the invention and should not be taken as an acknowledgment or in any form implied that the information constitutes the prior art already known to one of ordinary skill in the art.

SUMMARY OF THE INVENTION

Object of the Invention

The invention aims to provide a pyrimidine derivative and a preparation method and a use thereof.

The pyrimidine derivative shows an excellent CDK-inhibiting effect and action.

Technical Solutions

In order to achieve the object of the invention, provided is a pyrimidine derivative, which is selected from a compound represented by Formula (I), or a tautomer, an enantiomer, a diastereomer, a mesomer, a racemate, or a mixture thereof, or a pharmaceutically acceptable salt or prodrug thereof:

Formula (I)

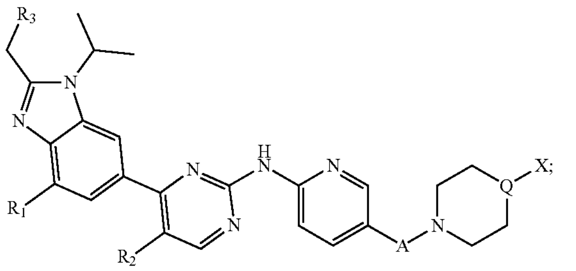

wherein $R_1$ and $R_2$ are each independently selected from fluorine or chlorine;

$R_3$ is selected from hydrogen, fluorine, or hydroxyl;

A is selected from methylene or a covalent bond;

Q is selected from a carbon atom or a nitrogen atom, wherein in case Q is a carbon atom, X is $—NR_4R_6$;

in case Q is a nitrogen atom and $R_3$ is hydrogen, X is $—R_5$;

in case Q is a nitrogen atom and $R_3$ is fluorine or hydroxyl, X is $C_1$-$C_3$ alkyl, $C_3$-$C_7$ cycloalkyl, or $R_5$;

$R_4$ is selected from hydrogen or $C_1$-$C_3$ alkyl;

$R_5$ is

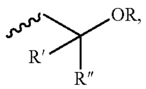

in which R, R', and R" are each independently selected from hydrogen or $C_1$-$C_3$ alkyl;

$R_6$ is $C_1$-$C_3$ alkyl, $C_3$-$C_7$ cycloalkyl, or $R_5$.

In one possible embodiment, in the compound represented by Formula (I), when Q is a nitrogen atom and $R_3$ is hydrogen, R, R', and R" in $R_5$ are each independently selected from hydrogen or methyl.

In one possible embodiment, in the compound represented by Formula (I), when Q is a nitrogen atom and $R_3$ is fluorine or hydroxyl, X is ethyl or $R_5$, and R, R', and R" in $R_5$ are each independently selected from hydrogen or methyl.

In one possible embodiment, in the compound represented by Formula (I), when Q is a carbon atom, $R_4$ is hydrogen or methyl, $R_6$ is methyl, ethyl, or $R_5$, and R, R', and R" in $R_5$ are each independently selected from hydrogen or methyl.

In one possible embodiment, in the compound represented by Formula (I), both $R_1$ and $R_2$ are fluorine, $R_3$ is hydrogen, A is selected from methylene or a covalent bond, Q is a nitrogen atom, and R, R', and R" in $R_5$ are each independently selected from hydrogen or methyl.

In one possible embodiment, in the compound represented by Formula (I), both $R_1$ and $R_2$ are fluorine, $R_3$ is fluorine, A is selected from methylene or a covalent bond, Q is a nitrogen atom, and X is ethyl.

In one possible embodiment, in the compound represented by Formula (I), both $R_1$ and $R_2$ are fluorine, $R_3$ is hydrogen or fluorine, A is selected from methylene or a covalent bond, Q is a carbon atom, $R_4$ is hydrogen or methyl, and $R_6$ is methyl, ethyl, or hydroxyethyl.

In one possible embodiment, the compound represented by Formula (I) is selected from the compounds with the following structures: Compound No. Compound ID Compound structure

| Compound No. | Compound ID | Compound structure |
|---|---|---|
| 1 | 1963 | 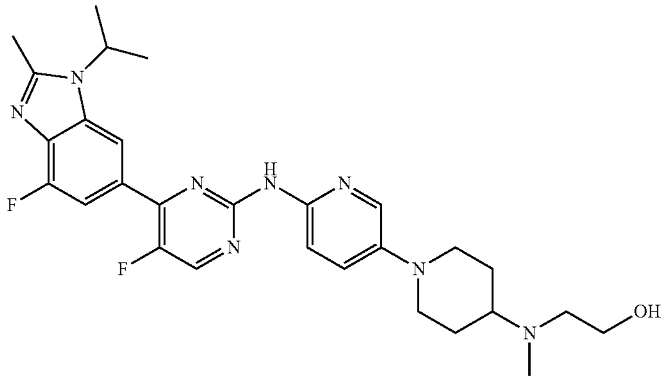 [SMILES: Cc1nc2c(F)cc(-c3nc(Nc4ccc(N5CCC(N(C)CCO)CC5)cn4)ncc3F)cc2n1C(C)C] |
| 2 | 1964 | 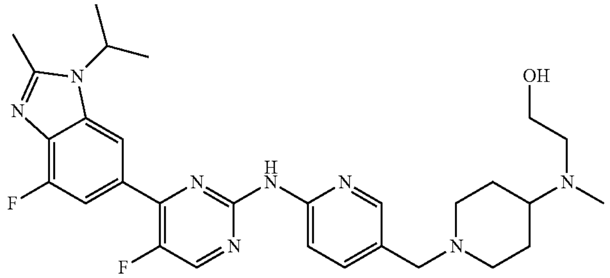 [SMILES: Cc1nc2c(F)cc(-c3nc(Nc4ccc(CN5CCC(N(C)CCO)CC5)cn4)ncc3F)cc2n1C(C)C] |
| 3 | 1967 | 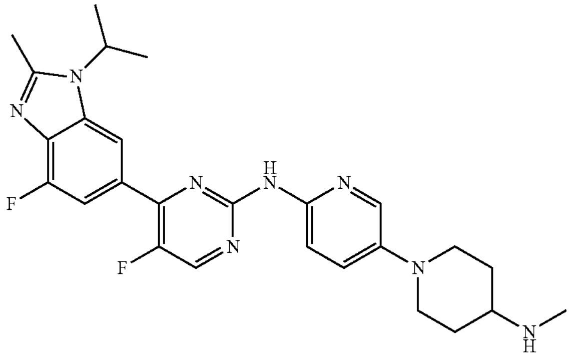 [SMILES: CNC1CCN(c2ccc(Nc3ncc(F)c(-c4cc(F)c5nc(C)n(C(C)C)c5c4)n3)nc2)CC1] |
| 4 | 1975 | 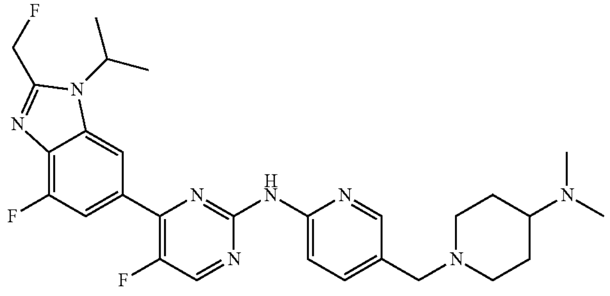 [SMILES: CC(C)n1c(CF)nc2c(F)cc(-c3nc(Nc4ccc(CN5CCC(N(C)C)CC5)cn4)ncc3F)cc21] |

-continued
| Compound No. | Compound ID | Compound structure |
|---|---|---|
| 5 | 1978 | 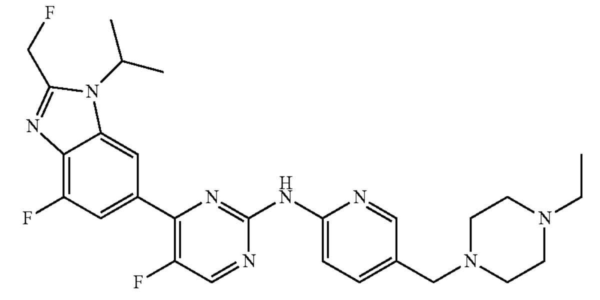 [SMILES: CCN1CCN(Cc2ccc(Nc3ncc(F)c(-c4cc(F)c5nc(CF)n(C(C)C)c5c4)n3)nc2)CC1] |
| 6 | 1979 | 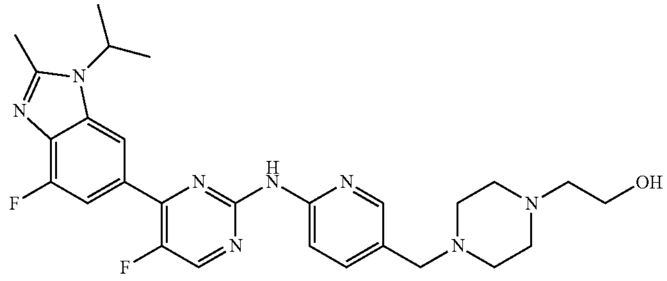 [SMILES: Cc1nc2c(F)cc(-c3nc(Nc4ccc(CN5CCN(CCO)CC5)cn4)ncc3F)cc2n1C(C)C] |
| 7 | 1983 | 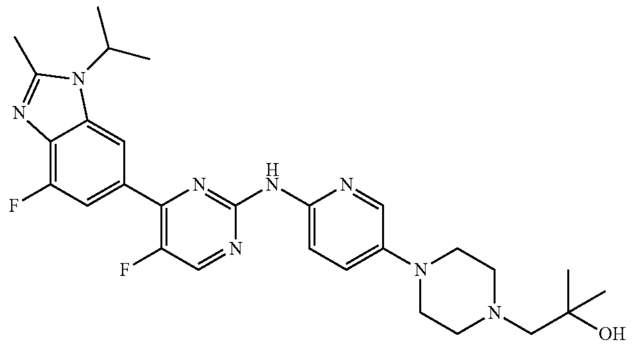 [SMILES: Cc1nc2c(F)cc(-c3nc(Nc4ccc(N5CCN(CC(C)(C)O)CC5)cn4)ncc3F)cc2n1C(C)C] |
| 8 | 1984 | 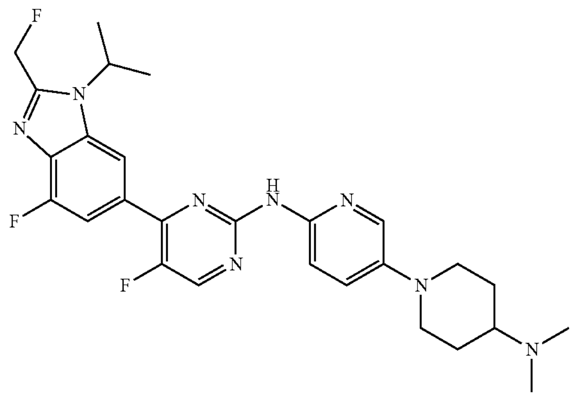 [SMILES: CC(C)n1c(CF)nc2c(F)cc(-c3nc(Nc4ccc(N5CCC(N(C)C)CC5)cn4)ncc3F)cc21] |

-continued
| Compound No. | Compound ID | Compound structure |
|---|---|---|
| 9 | 1985 | 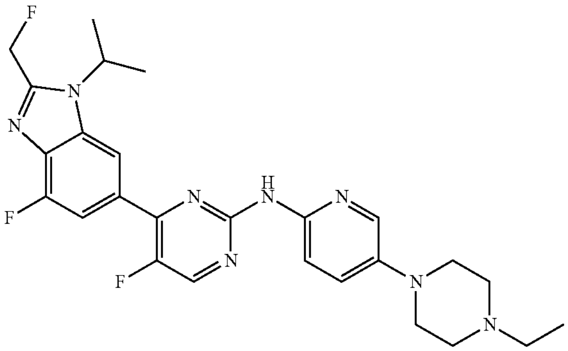 [SMILES: CCN1CCN(c2ccc(Nc3ncc(F)c(-c4cc(F)c5nc(CF)n(C(C)C)c5c4)n3)nc2)CC1] |
| 10 | 1986 | 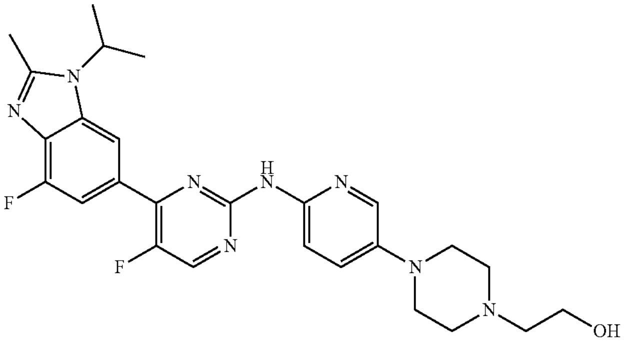 [SMILES: Cc1nc2c(F)cc(-c3nc(Nc4ccc(N5CCN(CCO)CC5)cn4)ncc3F)cc2n1C(C)C] |
| 11 | 1987 | 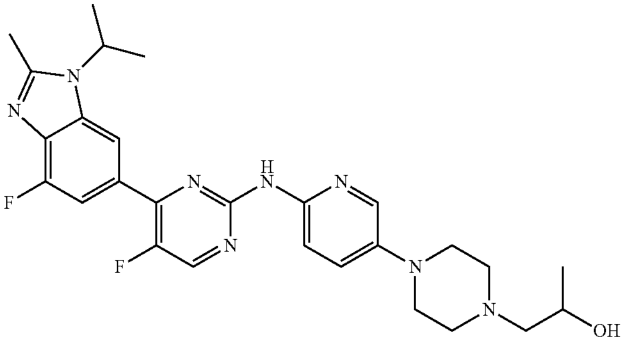 [SMILES: Cc1nc2c(F)cc(-c3nc(Nc4ccc(N5CCN(CC(C)O)CC5)cn4)ncc3F)cc2n1C(C)C] |
| 12 | 1988 | 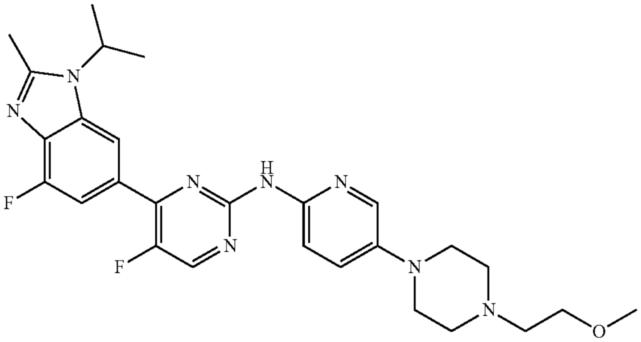 [SMILES: COCCN1CCN(c2ccc(Nc3ncc(F)c(-c4cc(F)c5nc(C)n(C(C)C)c5c4)n3)nc2)CC1] |

-continued
| Compound No. | Compound ID | Compound structure |
|---|---|---|
| 13 | 1990 | 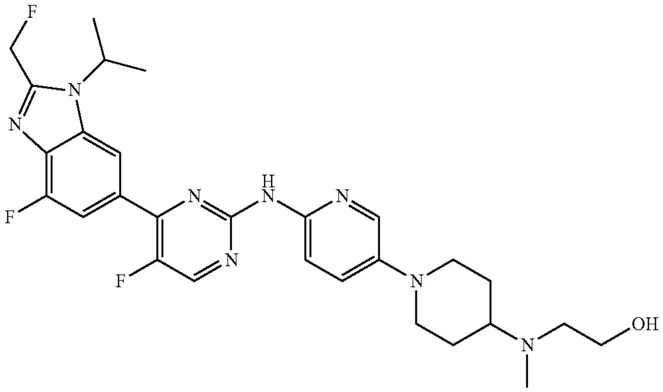 [SMILES: CC(C)n1c(CF)nc2c(F)cc(-c3nc(Nc4ccc(N5CCC(N(C)CCO)CC5)cn4)ncc3F)cc21] |
| 14 | 1994 | 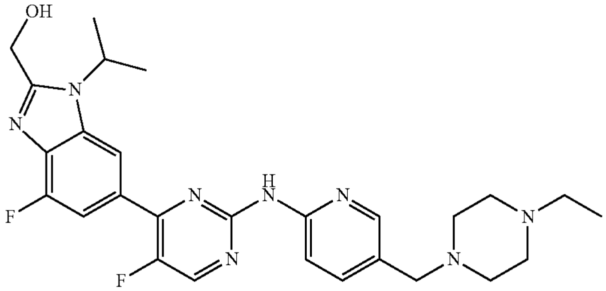 [SMILES: CCN1CCN(Cc2ccc(Nc3ncc(F)c(-c4cc(F)c5nc(CO)n(C(C)C)c5c4)n3)nc2)CC1] |
| 15 | 1995 | 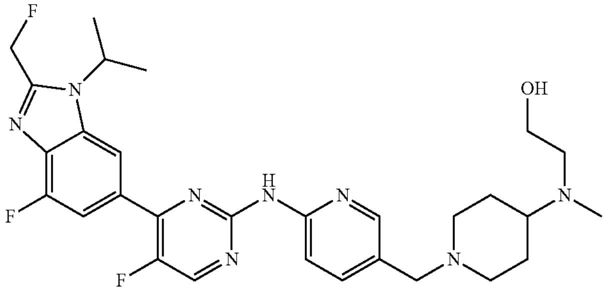 [SMILES: CC(C)n1c(CF)nc2c(F)cc(-c3nc(Nc4ccc(CN5CCC(N(C)CCO)CC5)cn4)ncc3F)cc21] |
| 16 | 1999 | 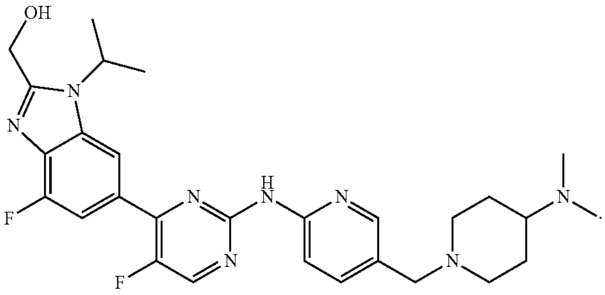 |

The invention also provides a method for preparing the pyrimidine derivative, the method being selected from any one of the following methods:

(1) Known Compounds I-A and I-B are cyclized to form benzimidazole I-C, I-C is converted to pinacol borate, which then undergoes Suzuki coupling reaction with I-D to form I-E, I-E finally undergoes Buchwald coupling reaction with the corresponding 2-aminopyridine to form the representative structure I;

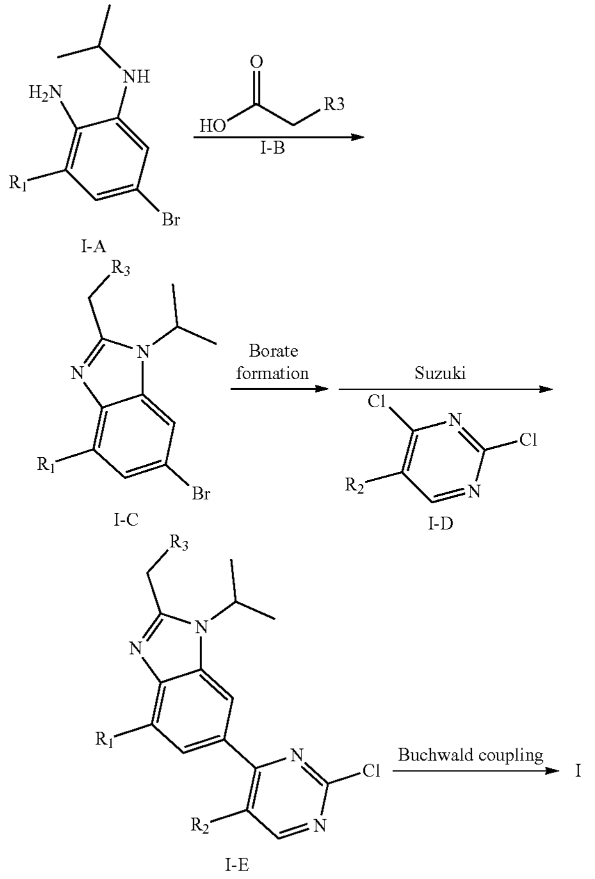

(2)

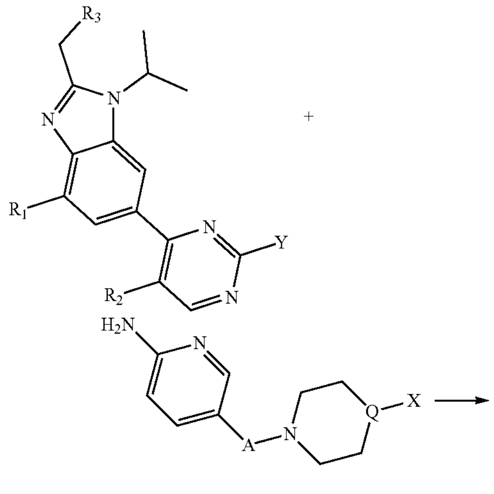

-continued

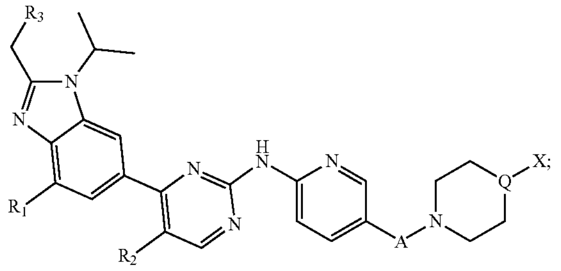

(3)

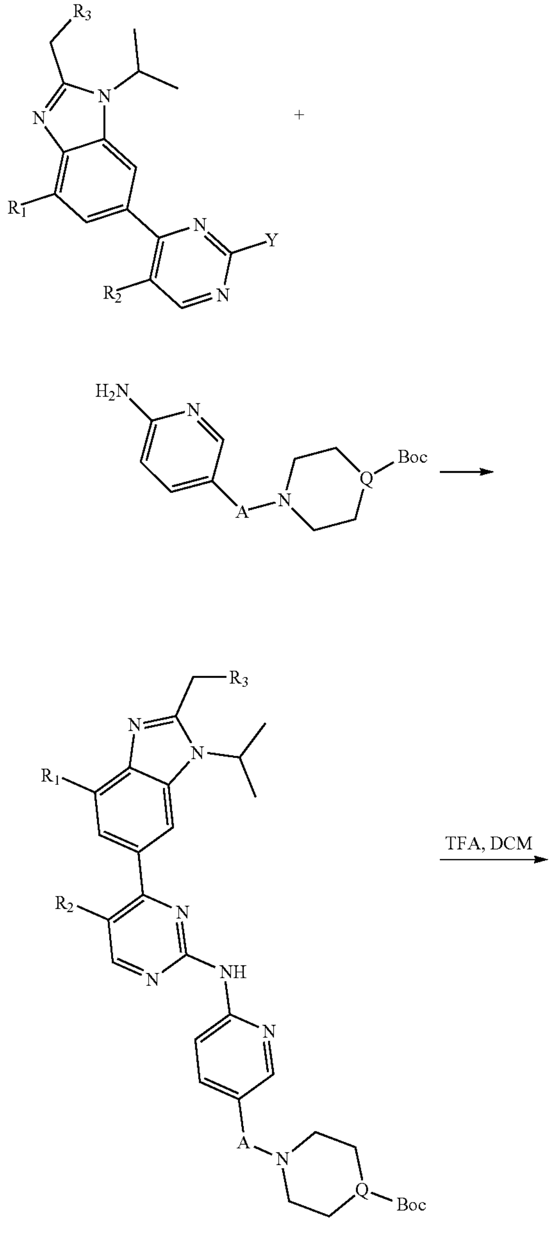

-continued

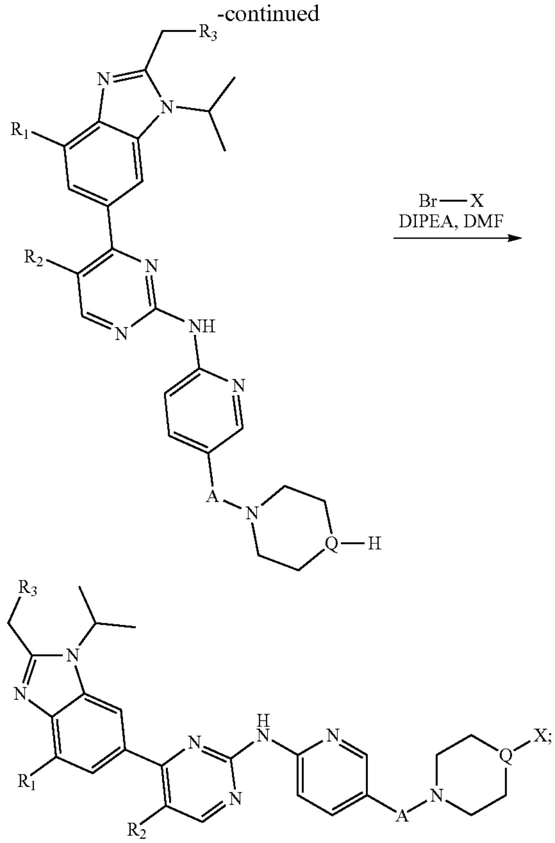

Wherein, $R_1$, $R_2$, $R_3$, A, Q, and X have the same meanings as the corresponding groups in the above pyrimidine derivative; Y is halogen.

The invention also provides a use of the pyrimidine derivative as an active ingredient in the preparation of a pharmaceutical composition.

In one possible embodiment, the pharmaceutical composition is a drug used for treating abnormal cell proliferative diseases, infections (e.g., viral infections such as herpes, HIV, fungal infection), inflammatory diseases (such as rheumatoid arthritis, osteoarthritis), autoimmune diseases (such as psoriasis, lupus, type I diabetes, diabetic nephropathy, multiple sclerosis, glomerulonephritis), cardiovascular diseases (such as myocardial infarction, stroke, atherosclerosis, postoperative vascular stenosis, restenosis) or neurodegenerative diseases (such as Alzheimer's disease, Parkinson's disease), and hematopoietic toxic diseases caused by radiation (such as myelosuppression, neutropenia, leukopenia, anemia).

In one possible embodiment, the treatment of abnormal cell proliferative diseases is the treatment of cancer; optionally, the cancer is selected from the group consisting of breast cancer, ovarian cancer, prostate cancer, melanoma, brain tumor (such as glioma with malignant astrocytes and oligodendroglioma components), esophageal cancer, gastric cancer, liver cancer, pancreatic cancer, colorectal cancer (such as colon cancer, rectal cancer), lung cancer (such as non-small cell lung cancer, small cell lung cancer, primary or metastatic squamous cancer), kidney cancer, skin cancer, glioblastoma, neuroblastoma, sarcoma, liposarcoma, osteochondroma, osteoma, osteosarcoma, seminoma, testicular tumor, uterine cancer (such as cervical cancer, endometrial cancer), head and neck tumor (such as maxillary bone cancer, laryngeal cancer, pharyngeal cancer, tongue cancer, oral cancer), multiple myeloma, malignant lymphoma (such as reticular cell sarcoma, lymphosarcoma, Hodgkin's lymphoma, mantle cell lymphoma), polycythemia vera, leukemia (such as acute myeloblastic leukemia, chronic myelocytic leukemia, acute lymphoblastic leukemia, chronic lymphocytic leukemia), thyroid tumor, ureteral tumor, bladder tumor, gallbladder cancer, cholangiocarcinoma, choriocarcinoma or pediatric tumor (such as Ewing sarcoma, Wilms sarcoma, rhabdomyosarcoma, angiosarcoma, embryonic testicular cancer, neuroblastoma, retinoblastoma, hepatoblastoma, nephroblastoma), and the like.

In one possible embodiment, the cancer is breast cancer or ovarian cancer.

The invention also provides a pharmaceutical composition, which comprises the pyrimidine derivative as an active ingredient and one or more pharmaceutically acceptable carriers, diluents or excipients.

In one possible embodiment, the pharmaceutical composition further comprises one or more other anticancer agents as active ingredients, which are selected from the group consisting of alkylating agents (such as cyclophosphamide, ifosfamide, melphalan, busulfan, nimustine, ranimustine, dacarbazine, temozolomide, nitrogen mustard hydrochloride, dibromomannitol), platinum complexing agents (such as cisplatin, carboplatin, oxaliplatin), metabolic antagonists (such as methotrexate, 5-fluorouracil, tegafur, gemcitabine, capecitabine, fulvestrant, pemetrexed), plant alkaloids (such as vincristine, vinblastine, vindesin, etoposide, docetaxel, paclitaxel, irinotecan, vinorelbine, mitoxantrone, vinflunine, topotecan), antibody drugs (such as trastuzumab, pertuzumab, rituximab, cetuximab, panitumumab, bevacizumab), hormonal anticancer agents (such as leuprorelin, goserelin, dutasteride, dexamethasone, tamoxifen), proteasome inhibitors (such as bortezomib, lenalidomide), aromatase inhibitors (such as exemestane, letrozole, anastrozole), VEGFR or EGFR inhibitors (such as sunitinib, sorafenib, imatinib, gefitinib, erlotinib, vandetanib, pazopanib, lapatinib), mTOR inhibitors (such as everolimus, sirolimus, zotarolimus), PI3K kinase inhibitors (such as BKM-120, XL-147, BEZ-235), B-Raf inhibitors (such as vemurafenib, GSK-2118436) or AKT inhibitors (such as perifosine, MK-2206), and the like; preferably aromatase inhibitors, more preferably letrozole or anastrozole.

The invention also provides a method for treating diseases, which comprises the step of administering an effective dose of the pyrimidine derivative to a subject in need of treatment of a disease, the diseases being selected from the group consisting of abnormal cell proliferative diseases, infections (e.g., viral infections such as herpes, HIV, fungal infection), inflammatory diseases (such as rheumatoid arthritis, osteoarthritis), autoimmune diseases (such as psoriasis, lupus, type I diabetes, diabetic nephropathy, multiple sclerosis, glomerulonephritis), cardiovascular diseases (such as myocardial infarction, stroke, atherosclerosis, postoperative vascular stenosis, restenosis) or neurodegenerative diseases (such as Alzheimer's disease, Parkinson's disease), and hematopoietic toxic diseases caused by radiation (such as myelosuppression, neutropenia, leukopenia, anemia).

In one possible embodiment, the abnormal cell proliferative diseases is cancer; optionally, the cancer is selected from the group consisting of breast cancer, ovarian cancer, prostate cancer, melanoma, brain tumor (such as glioma with malignant astrocytes and oligodendroglioma components), esophageal cancer, gastric cancer, liver cancer, pancreatic cancer, colorectal cancer (such as colon cancer, rectal cancer), lung cancer (such as non-small cell lung cancer, small cell lung cancer, primary or metastatic squamous cancer), kidney cancer, skin cancer, glioblastoma, neuroblastoma, sarcoma, liposarcoma, osteochondroma, osteoma, osteosarcoma, seminoma, testicular tumor, uterine cancer (such as cervical cancer, endometrial cancer), head and neck tumor (such as maxillary bone cancer, laryngeal cancer, pharyngeal cancer, tongue cancer, oral cancer), multiple myeloma, malignant lymphoma (such as reticular cell sarcoma, lymphosarcoma, Hodgkin's lymphoma, mantle cell lymphoma), polycythemia vera, leukemia (such as acute myeloblastic leukemia, chronic myelocytic leukemia, acute lymphoblastic leukemia, chronic lymphocytic leukemia), thyroid tumor, ureteral tumor, bladder tumor, gallbladder cancer, cholangiocarcinoma, choriocarcinoma or pediatric tumor (such as Ewing sarcoma, Wilms sarcoma, rhabdomyosarcoma, angiosarcoma, embryonic testicular cancer, neuroblastoma, retinoblastoma, hepatoblastoma, nephroblastoma), and the like.

In one possible embodiment, the cancer is breast cancer or ovarian cancer.

In one possible embodiment, the breast cancer is triple negative breast cancer.

In one possible embodiment, the method further comprises a use in combination with one or more other anticancer agents as active ingredients, which are selected from the group consisting of alkylating agents (such as cyclophosphamide, ifosfamide, melphalan, busulfan, nimustine, ranimustine, dacarbazine, temozolomide, nitrogen mustard hydrochloride, dibromomannitol), platinum complexing agents (such as cisplatin, carboplatin, oxaliplatin), metabolic antagonists (such as methotrexate, 5-fluorouracil, tegafur, gemcitabine, capecitabine, fulvestrant, pemetrexed), plant alkaloids (such as vincristine, vinblastine, vindesin, etoposide, docetaxel, paclitaxel, irinotecan, vinorelbine, mitoxantrone, vinflunine, topotecan), antibody drugs (such as trastuzumab, pertuzumab, rituximab, cetuximab, panitumumab, bevacizumab), hormonal anticancer agents (such as leuprorelin, goserelin, dutasteride, dexamethasone, tamoxifen), proteasome inhibitors (such as bortezomib, lenalidomide), aromatase inhibitors (such as exemestane, letrozole, anastrozole), VEGFR or EGFR inhibitors (such as sunitinib, sorafenib, imatinib, gefitinib, erlotinib, vandetanib, pazopanib, lapatinib), mTOR inhibitors (such as everolimus, sirolimus, zotarolimus), PI3K kinase inhibitors (such as BKM-120, XL-147, BEZ-235), B-Raf inhibitors (such as vemurafenib, GSK-2118436) or AKT inhibitors (such as perifosine, MK-2206), and the like; preferably aromatase inhibitors, more preferably letrozole or anastrozole.

The invention also provides a CDK inhibitor, which comprises the pyrimidine derivative.

In one possible embodiment, CDK includes CDK2, CDK4, or CDK6.

The invention also provides a method for preparing the CDK inhibitor, the method comprising the steps of preparing the pyrimidine derivative according to one of claims 1-4 using the preparation method described above.

The invention also provides a use of the CDK inhibitor as an active ingredient in the preparation of a pharmaceutical composition.

In one possible embodiment, the pharmaceutical composition is a drug used for treating abnormal cell proliferative diseases, infections (e.g., viral infections such as herpes, HIV, fungal infection), inflammatory diseases (such as rheumatoid arthritis, osteoarthritis), autoimmune diseases (such as psoriasis, lupus, type I diabetes, diabetic nephropathy, multiple sclerosis, glomerulonephritis), cardiovascular diseases (such as myocardial infarction, stroke, atherosclerosis, postoperative vascular stenosis, restenosis), neurodegenerative diseases (such as Alzheimer's disease, Parkinson's disease), and hematopoietic toxic diseases caused by radiation (such as myelosuppression, neutropenia, leukopenia, anemia).

In one possible embodiment, the treatment of the abnormal cell proliferative disease is the treatment of cancer.

In one possible embodiment, the cancer is selected from the group consisting of breast cancer, ovarian cancer, prostate cancer, melanoma, brain tumor (such as glioma with malignant astrocytes and oligodendroglioma components), esophageal cancer, gastric cancer, liver cancer, pancreatic cancer, colorectal cancer (such as colon cancer, rectal cancer), lung cancer (such as non-small cell lung cancer, small cell lung cancer, primary or metastatic squamous cancer), kidney cancer, skin cancer, glioblastoma, neuroblastoma, sarcoma, liposarcoma, osteochondroma, osteoma, osteosarcoma, seminoma, testicular tumor, uterine cancer (such as cervical cancer, endometrial cancer), head and neck tumor (such as maxillary bone cancer, laryngeal cancer, pharyngeal cancer, tongue cancer, oral cancer), multiple myeloma, malignant lymphoma (such as reticular cell sarcoma, lymphosarcoma, Hodgkin's lymphoma, mantle cell lymphoma), polycythemia vera, leukemia (such as acute myeloblastic leukemia, chronic myelocytic leukemia, acute lymphoblastic leukemia, chronic lymphocytic leukemia), thyroid tumor, ureteral tumor, bladder tumor, gallbladder cancer, cholangiocarcinoma, choriocarcinoma, or pediatric tumor (such as Ewing sarcoma, Wilms sarcoma, rhabdomyosarcoma, angiosarcoma, embryonic testicular cancer, neuroblastoma, retinoblastoma, hepatoblastoma, nephroblastoma).

In one possible embodiment, the cancer is breast cancer or ovarian cancer.

In one possible embodiment, the breast cancer is triple negative breast cancer.

A pharmaceutical composition comprises the CDK inhibitor as an active ingredient, and one or more pharmaceutically acceptable carriers, diluents or excipients.

In one possible embodiment, the pharmaceutical composition further comprises one or more other anticancer agents as active ingredients, which are selected from the group consisting of alkylating agents (such as cyclophosphamide, ifosfamide, melphalan, busulfan, nimustine, ranimustine, dacarbazine, temozolomide, nitrogen mustard hydrochloride, dibromomannitol), platinum complexing agents (such as cisplatin, carboplatin, oxaliplatin), metabolic antagonists (such as methotrexate, 5-fluorouracil, tegafur, gemcitabine, capecitabine, fulvestrant, pemetrexed), plant alkaloids (such as vincristine, vinblastine, vindesin, etoposide, docetaxel, paclitaxel, irinotecan, vinorelbine, mitoxantrone, vinflunine, topotecan), antibody drugs (such as trastuzumab, pertuzumab, rituximab, cetuximab, panitumumab, bevacizumab), hormonal anticancer agents (such as leuprorelin, goserelin, dutasteride, dexamethasone, tamoxifen), proteasome inhibitors (such as bortezomib, lenalidomide), aromatase inhibitors (such as exemestane, letrozole, anastrozole), VEGFR or EGFR inhibitors (such as sunitinib, sorafenib, imatinib, gefitinib, erlotinib, vandetanib, pazopanib, lapatinib), mTOR inhibitors (such as everolimus, sirolimus, zotarolimus), PI3K kinase inhibitors (such as BKM-120, XL-147, BEZ-235), B-Raf inhibitors (such as vemurafenib, GSK-2118436) or AKT inhibitors (such as perifosine, MK-2206), and the like; one or more other anticancer agents are preferably aromatase inhibitors, more preferably letrozole or anastrozole.

The invention also provides a method for inhibiting CDK activity, the method comprising the step of administering an effective dose of the pyrimidine derivative to a subject in need of inhibiting CDK activity.

Beneficial Effects

The pyrimidine derivative of the invention shows an excellent CDK-inhibiting effect and action, especially on CDK2, CDK4, and CDK6; and gives a lower IC50 value compared with Abemaciclib.

DETAILED DESCRIPTION OF THE INVENTION

In order to make the objects, technical solutions and advantages of the invention clearer, the technical solutions of the invention will be described clearly and completely in connection with the examples, obviously, the described examples are some of the examples of the present invention, but not all of them. Based on the examples of the present invention, all other examples obtained by those of ordinary skill in the art without creative work are within the scope of the present invention.

In addition, in order to better explain the present invention, a lot of specific details are given in the following embodiments. It will be understood by those skilled in the art that the present invention may be practiced without certain specific details. In some embodiments, materials, elements, methods, means, etc., well known to those skilled in the art, are not described in detail so as to highlight the spirit of the present invention.

Throughout the specification and claims, the term "comprising" or variations thereof, such as "including" or "containing", will be understood to include the stated elements or components and not to exclude other elements or other components, unless expressly indicated otherwise.

The term "alkyl" refers to a saturated aliphatic hydrocarbon group including a linear or branched group containing 1 to 20 carbon atoms, preferably alkyl containing 1 to 10 carbon atoms, more preferably alkyl containing 1 to 6 carbon atoms, most preferably alkyl containing 1 to 4 carbon atoms, and most preferably methyl. Non-limiting examples thereof include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched chain isomers thereof. More preferred is a lower alkyl group containing 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group may be substituted or unsubstituted, in case of being substituted, the substituent may be substituted at any available attachment point, and is preferably one or more independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, oxo, amino, haloalkyl, hydroxyalkyl, carboxyl, or a carboxylate group.

The term "cycloalkyl" refers to a saturated or partially unsaturated monocyclic or polycyclic hydrocarbon ring substituent, which contains 3 to 20 carbon atoms, preferably 3 to 12 carbon atoms, more preferably 3 to 10 carbon atoms, most preferably 3 to 6 carbon atoms in the cycloalkyl ring, and most preferably cyclopropyl or cyclopentyl. Non-limiting examples of a monocyclic alkyl group include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, and preferably cyclopropyl and cyclopentyl. Polycyclic alkyl groups include spiro, fused and bridged cycloalkyl groups. The cycloalkyl group may be substituted or unsubstituted, and in case of being substituted, the substituent may be preferably one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, oxo, amino, haloalkyl, hydroxyalkyl, carboxyl, or a carboxylate group.

The term "alkoxy" refers to —O-(alkyl) and —O-(unsubstituted cycloalkyl), wherein alkyl and cycloalkyl are as defined above. Non-limiting examples include methoxy, ethoxy, propoxy, butoxy, cyclopropyloxy, cyclobutyloxy, cyclopentyloxy, cyclohexyloxy, and the like. The alkoxy group may be substituted or unsubstituted, and in case of being substituted, the substituent may be preferably one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, amino, haloalkyl, hydroxyalkyl, carboxyl, or a carboxylate group.

"Haloalkyl" refers to alkyl substituted by one or more halogens, wherein alkyl is as defined above.

"Hydroxyl" refers to the —OH group.

"Hydroxyalkyl" refers to alkyl substituted by hydroxyl, wherein alkyl is as defined above.

"Halogen" refers to fluorine, chlorine, bromine or iodine, preferably fluorine or iodine.

"Amino" refers to $—NH_2$.

"Cyano" refers to —CN.

"Nitro" refers to $—NO_2$.

"Oxo" refers to =O.

"Carboxyl" refers to —C(O)OH.

"Carboxylate group" refers to —C(O)O (alkyl) or (cycloalkyl), wherein alkyl and cycloalkyl are as defined above.

"Optional" or "optionally" means that the event or environment described subsequently may, but not necessarily, occur, which includes the case where this event or environment may or may not occur. For example, "heterocycloalkyl group optionally substituted by alkyl" means that alkyl may but not necessarily exist, which includes both the case where heterocycloalkyl is substituted by alkyl and the case where heterocycloalkyl is not substituted by alkyl.

"Substituted" means that one or more hydrogen atoms in a group, preferably up to 5, more preferably 1 to 3 hydrogen atoms, are each independently substituted by a corresponding number of substituents. It is self-evident that substituents are only in their possible chemical positions, and those skilled in the art can determine (through experiments or theories) possible or impossible substitutions without making too much effort. For example, an amino or hydroxyl group with free hydrogen may be unstable when binding to a carbon atom with an unsaturated (e.g., olefinic) bond.

Example 1 Synthesis of Compound 1979

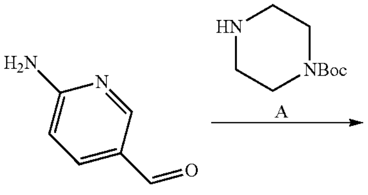

1

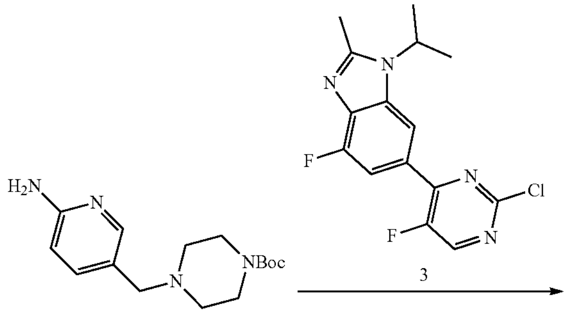

3

2

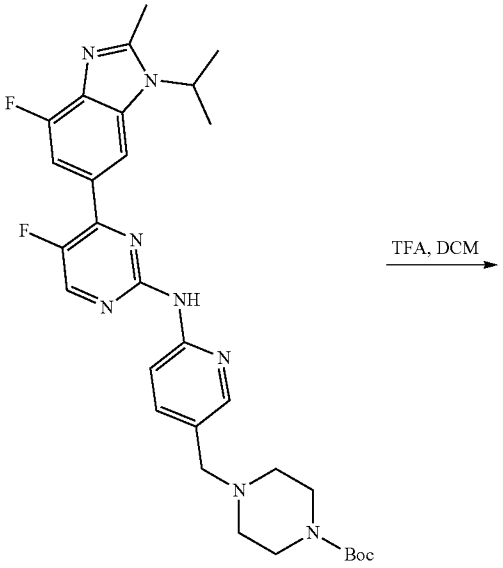

4

-continued

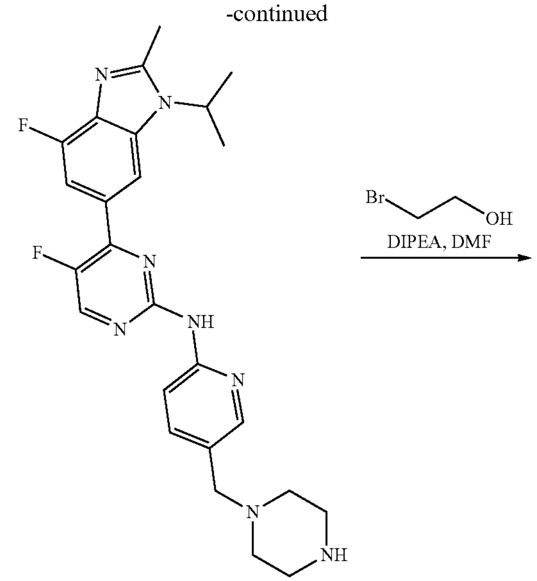

5

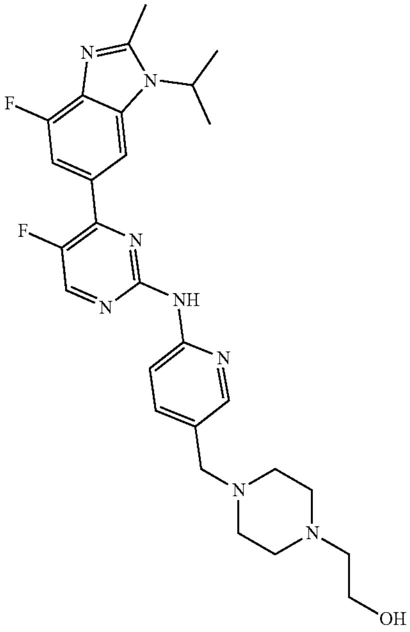

1979

Synthesis of Compound 2

Compound 1 (3.0 g, 24.6 mmol) and compound A (5.03 g, 27.0 mmol) were dissolved in THF (80 mL) at room temperature, followed by addition of 3 drops of acetic acid, the solution was stirred for half an hour, then sodium borohydride acetate (15.6 g, 73.8 mmol) was added in batches, and the mixture was stirred at room temperature over night. After addition of 50 mL of sodium carbonate aqueous solution and extraction twice with ethyl acetate, the organic phases were combined, dried with sodium sulfate, filtered and concentrated to yield the crude Compound 2 (7.8 g).

Synthesis of Compound 4

The crude Compound 2 (7.8 g, 26.7 mmol) and Compound 3 (7.17 g, 22.3 mmol) were dissolved in 1,4-dioxane (150 mL) at room temperature, followed by addition of $Pd_2(dba)_3$ (2.0 g, 2.23 mmol), Xantphos (2.5 g, 4.46 mmol), and potassium carbonate (4.6 g, 33.45 mmol), then the system was allowed to 4-time nitrogen replacement and heated to reflux for 5 hours. After addition of 500 mL of water and extraction 4 times with dichloromethane, the organic phases were combined, dried with sodium sulfate, filtered and concentrated to yield the crude Compound 4 (13 g), which was then pulped with ethyl acetate (150 mL) for half an hour, filtered and dried to obtain Compound 4 (13 g).

Synthesis of Compound 5

Compound 4 (13.0 g, 25 mmol) was dissolved in dichloromethane (50 mL) at room temperature, followed by addition of 15 mL of trifluoroacetic acid, the solution was stirred at room temperature over night. After concentration, adjustment of pH to be 8-9 with saturated sodium carbonate solution, and 5-time extraction with dichloromethane, the organic phases were combined, dried and concentrated, subject to column chromatography, and eluted with methanol/dichloromethane gradient to yield Compound 5 (6 g) with the volume ratio of methanol adjusted to be 0-10%.

Synthesis of Compound 1979

Compound 5 (6 g, 12.5 mmol) and bromoethanol (1.9 g, 15.1 mmol) were dissolved in DMF (50 mL) at room temperature, followed by addition of DIPEA (4.9 g, 37.7 mmol) and potassium iodide (catalytic amount), the solution was heated to 80° C. for reacting for 5 hours. When the reaction was complete as detected via LC-MS, concentration was carried out and DMF was removed, followed by column chromatography and elution with methanol/dichloromethane gradient to yield the crude Compound 1979 (3.5 g) with the volume ratio of methanol adjusted to be 0-10%, which was then pulped with 100 mL of ethyl acetate for half an hour and filtered to obtain Compound 1979 (3.0 g) (LCMS, M+1:523).

Example 2 Synthesis of Compound 1963

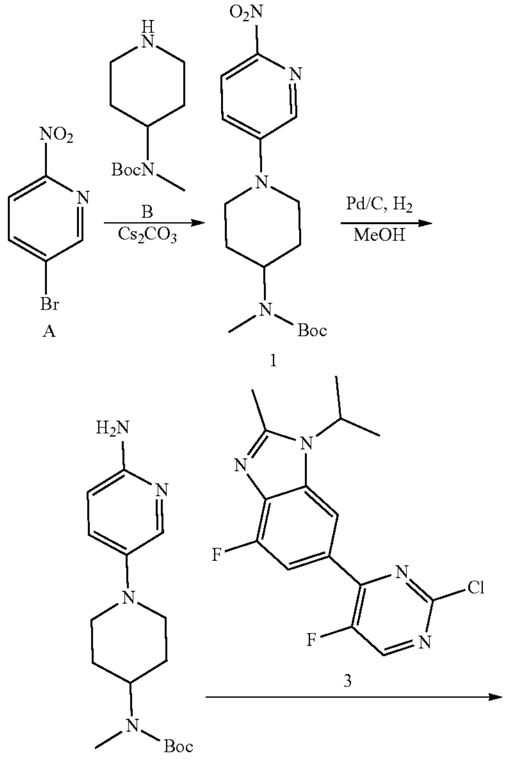

A

1

2

3

-continued

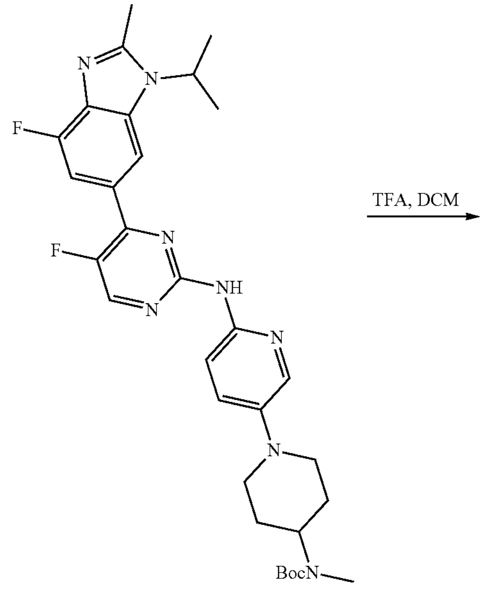

4

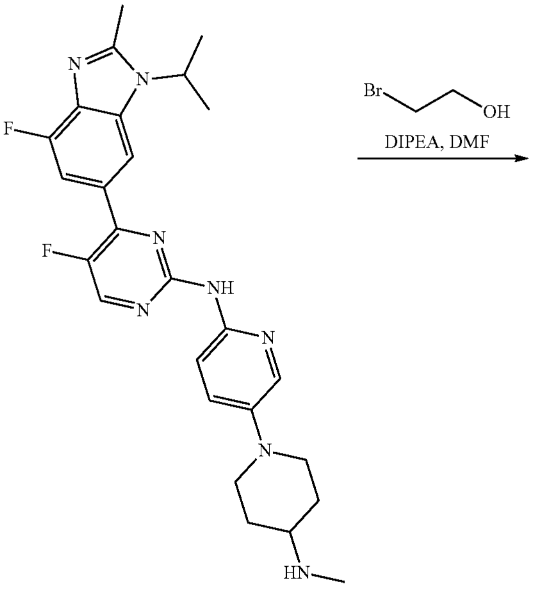

5

-continued

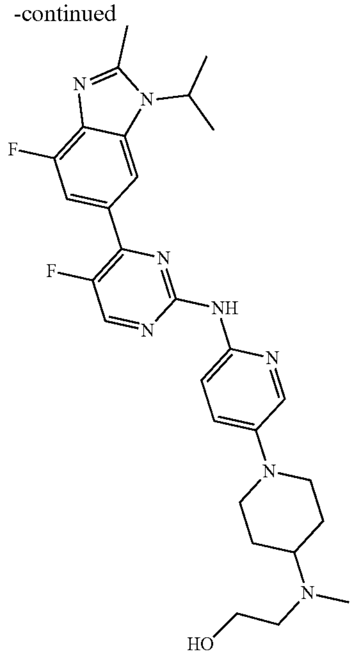

1963

Synthesis of Compound 1

Compound A (7.9 g, 39 mmol) and Compound B (10 g, 47 mmol) were dissolved in DMF (50 m) at room temperature, followed by addition of cesium carbonate (19 g, 58 mmol), the solution was heated to 120-125 for reacting for 5 hours. After cooling down to room temperature and addition of 200 mL of water, the resulting mixture was stirred for half an hour, filtered, dried, pulped with a mixed solvent of ethyl acetate and petroleum ether for half an hour and additionally filtered, to yield the crude Compound 1 (8.3 g).

Synthesis of Compound 2

The crude Compound 1 (8.3 g) was dissolved in methanol (150 m) at room temperature, followed by addition of $Pd_2C$ (1.6 g), then the system was allowed to 3-time hydrogen replacement and stirred at room temperature over night. After filtration, the mother liquor was concentrated to yield the crude product, which was then pulped with the mixed solvent of ethyl acetate and petroleum ether for half an hour, and additionally filtered to obtain Compound 2 (5.3 g).

Synthesis of Compound 4

Compound 2 (5.3 g, 17.2 mmol) and Compound 3 (5.1 g, 15.8 mmol) were dissolved in 1,4-dioxane (50 mL) at room temperature, followed by addition of $Pd_2(dba)_3$ (0.72 g, 0.8 mmol), Xantphos (0.9 g, 1.7 mmol), and potassium carbonate (3.2 g, 72 mmol), then the system was allowed to 4-time nitrogen replacement and heated to reflux for 5 hours. After addition of 100 mL of water and filtration, the solid was pulped with ethanol (150 mL) for half an hour, filtered and dried to obtain Compound 4 (8.4 g).

Synthesis of Compound 5

Compound 4 (8.4 g, 14.2 mmol) was dissolved in dichloromethane (50 mL) at room temperature, followed by addition of 15 mL of trifluoroacetic acid, the solution was stirred at room temperature over night. After concentration, adjustment of pH to be 8-9 with saturated sodium carbonate solution, and 5-time extraction with dichloromethane, the organic phases were combined, dried and concentrated, subject to column chromatography, and eluted with 0-10% methanol/dichloromethane to obtain Compound 5 (5 g).

Synthesis of Compound 1963

Compound 5 (3.2 g, 6.5 mmol) and bromoethanol (0.9 g, 7.8 mmol) were dissolved in DMF (30 mL) at room temperature, followed by addition of DIPEA (1.72 g, 13.3 mmol) and potassium iodide (catalytic amount), the solution was heated to 80° C. for reacting for 5 hours. When the reaction was complete as detected via LC-MS, concentration was carried out and DMF was removed, followed by column chromatography and elution with 0-10% methanol/dichloromethane to obtain the crude Compound 1963 (1.6 g), which was then pulped with 100 mL of ethyl acetate for half an hour and filtered to give Compound 1963 (1.3 g) (LCMS, M+1:537).

Example 3 Synthesis of Compound 1984

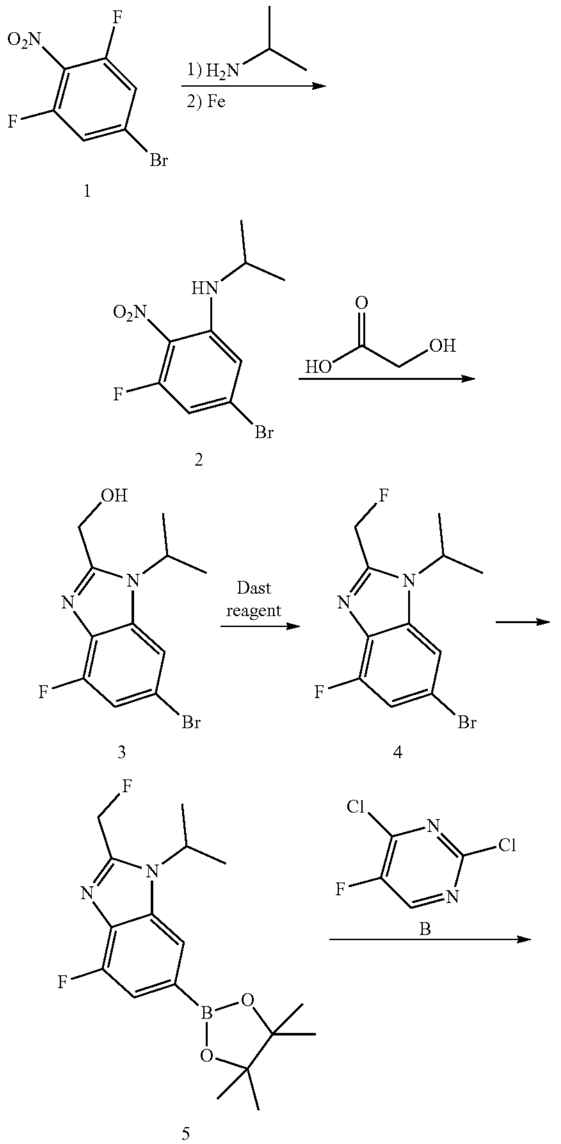

-continued

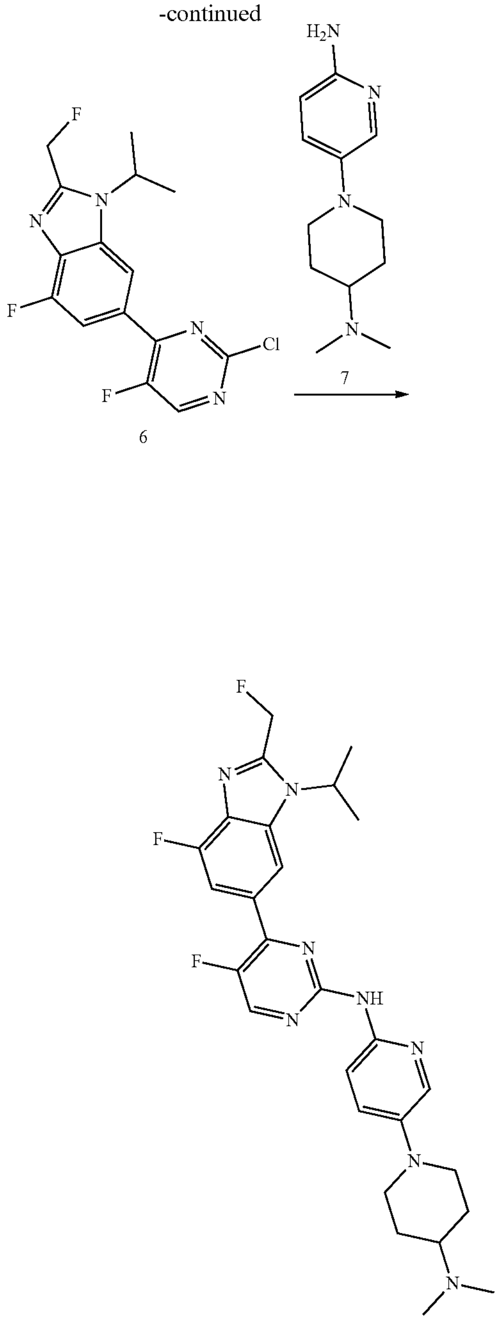

6

7

1984

Synthesis of Compound 2

Compound 1 (18 g, 76 mmol) and cesium carbonate (24.6 g, 76 mmol) were added to THF (90 g) at room temperature, the temperature was cooled to 0-5° C. and controlled below 10° C., isopropylamine (4.5 g, 76 mmol) was added dropwise, and the reaction was carried out at room temperature for 5 hours. When the reaction was complete as detected via LC-MS, filtration and concentration were carried out to yield 22 g of reddish-brown solid. The obtained reddish-brown solid (22 g, 79 mmol) was added to the mixed solution of ethanol (80 mL) and water (20 mL), followed by addition of ammonium chloride (7.94 g, 148 mmol) and iron powder (25.3 g, 454 mmol), the mixture was warmed to reflux for 1 hour. When the reaction was complete as detected via LC-MS, water and EA were added with stirring followed by filtration, the resultant aqueous phase was subject to extraction with EA, dryness, concentration, column chromatography and elution with PE to obtain Compound 2 (brown liquid, 12.1 g).

Synthesis of Compound 3

Compound 2 (3 g, 12.14 mmol) was added to a solution of water (12 mL) and concentrated hydrochloric acid (6 mL), followed by addition of glycolic acid (4.6 g, 60.7 mmol), the solution was heated to reflux for reacting for 3 hours. When the reaction was complete as detected via LC-MS, the resulting mixture was cooled down, adjusted to a pH of about pH 8-9 with sodium carbonate solution, extracted with EA, dried and concentrated to yield Compound 3 as yellow solid (3.1 g).

Synthesis of Compound 4

Compound 3 (3 g, 10.44 mmol) was added to DCM (30 mL), the temperature was cooled down to 0-5° C., the Dast reagent (2.02 g, 12.54 mmol) was added dropwise with controlled temperature below 10° C., and the solution was warmed to room temperature and then to reflux for reaction, after further addition of the Dast reagent (0.6 g), the reaction was kept under refluxing for 24 hours. When most of raw materials were converted as detected via LC-MS, the resulting mixture was cooled down, adjusted to a pH of 8 with sodium bicarbonate, extracted with DCM, subject to column chromatography, and eluted with 0-5% EA to yield Compound 4 as yellow solid (0.9 g).

One-Pot Synthesis of Compound 5 and Compound 6

Compound 4 (0.92 g, 3.2 mmol), bis(pinacolato)diboron (0.96 g, 3.8 mmol), potassium acetate (0.62 g, 6.36 mmol) and Pd(dppf)$Cl_2$ (0.22 g, 0.64 mmol) were added to dioxane (30 mL) successively, the solution was heated to reflux for reacting for 2 hours under nitrogen protection. When the reaction was complete as detected via LC-MS, cooling was carried out, sodium carbonate (0.67 g, 6.36 mmol) and Compound B (0.53 g, 3.2 mmol) were added to the reaction system of Compound 5, followed by addition of Pd(dppf)$Cl_2$ (0.11 g, 0.32 mmol) and water (7 mL), the mixture was heated to 80-90° C. for reacting for 2 hours under nitrogen protection. When the reaction was complete as detected via LC-MS, the resulting mixture was cooled down, added with water, extracted with EA, dried, concentrated, subject to column chromatography, eluted with 0-15% EA to yield Compound 6 as yellow solid (0.62 g).

Synthesis of Compound 1984

Compound 6 (0.15 g, 0.44 mmol) and Compound 7 (0.11 g, 0.484 mmol) were added to dioxane, followed by addition of $Pd_2(dba)_3$ (44.4 mg, 0.044 mmol), Xantphos (51 mg, 0.088 mmol), and potassium carbonate (91.2 mg, 0.66 mmol), the solution was heated to reflux for reaction under nitrogen protection. When the reaction was complete as detected via LC-MS, the resulting mixture was cooled down, added with water, extracted with DCM, scraped on the plate to yield compound 1984 as yellow solid (98 mg) (LCMS, M+1:525).

Example 4: Other Preparation Examples
Other compound preparation examples include:
| Compound ID | Compound structure | Synthesis method | M + 1 |
|---|---|---|---|
| 1967 | 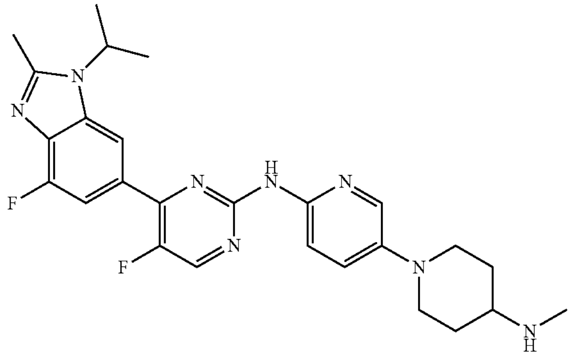 [SMILES: CNC1CCN(c2ccc(Nc3ncc(F)c(-c4cc(F)c5nc(C)n(C(C)C)c5c4)n3)nc2)CC1] | Reference to Example 2 | 493 |
| 1978 | 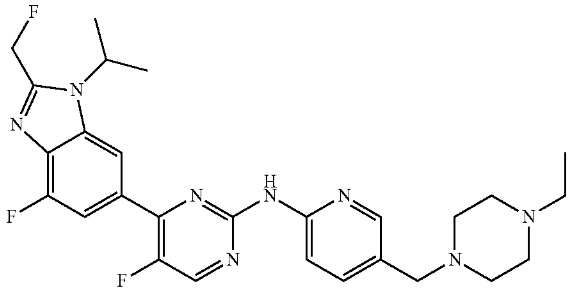 [SMILES: CCN1CCN(Cc2ccc(Nc3ncc(F)c(-c4cc(F)c5nc(CF)n(C(C)C)c5c4)n3)nc2)CC1] | Reference to Example 3 | 525 |
| 1985 | 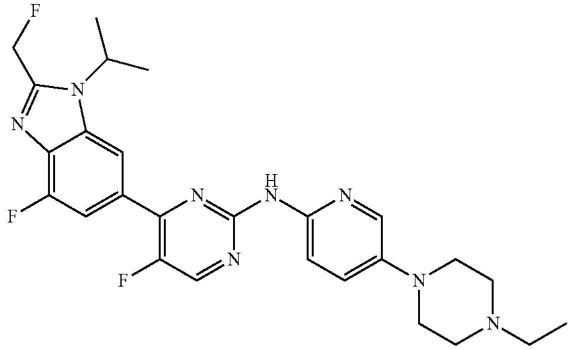 [SMILES: CCN1CCN(c2ccc(Nc3ncc(F)c(-c4cc(F)c5nc(CF)n(C(C)C)c5c4)n3)nc2)CC1] | Reference to Example 3 | 511 |
| 1986 | 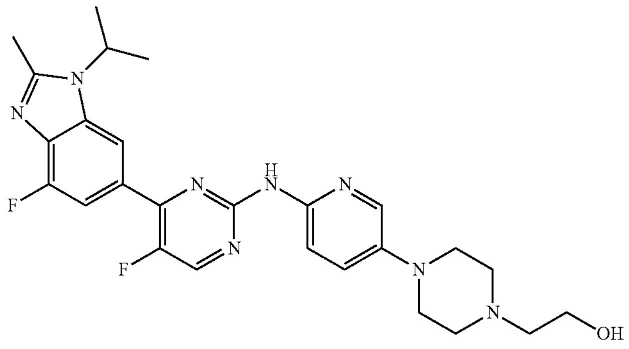 [SMILES: Cc1nc2c(F)cc(-c3nc(Nc4ccc(N5CCN(CCO)CC5)cn4)ncc3F)cc2n1C(C)C] | Reference to Example 1 | 509 |

-continued
| Compound ID | Compound structure | Synthesis method | M + 1 |
|---|---|---|---|
| 1988 | 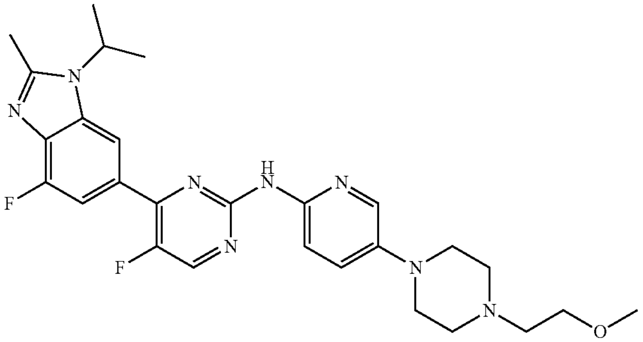 [SMILES: COCCN1CCN(c2ccc(Nc3ncc(F)c(-c4cc(F)c5nc(C)n(C(C)C)c5c4)n3)nc2)CC1] | Reference to Example 1 | 523 |
| 1999 | 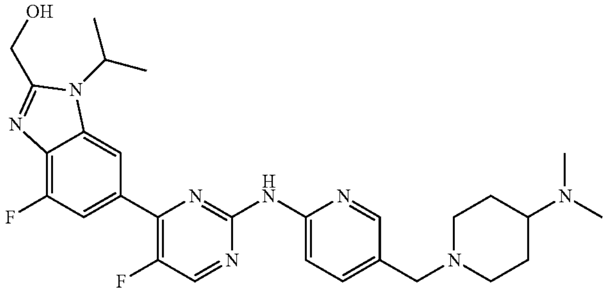 [SMILES: CC(C)n1c(CO)nc2c(F)cc(-c3nc(Nc4ccc(CN5CCC(N(C)C)CC5)cn4)ncc3F)cc21] | Reference to Example 4 | 524 |
| 1994 | 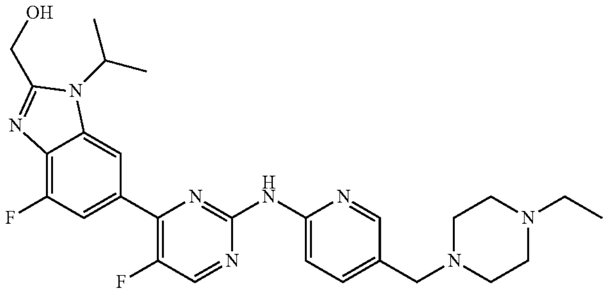 [SMILES: CCN1CCN(Cc2ccc(Nc3ncc(F)c(-c4cc(F)c5nc(CO)n(C(C)C)c5c4)n3)nc2)CC1] | Reference to Example 3 | 524 |
| 1995 | 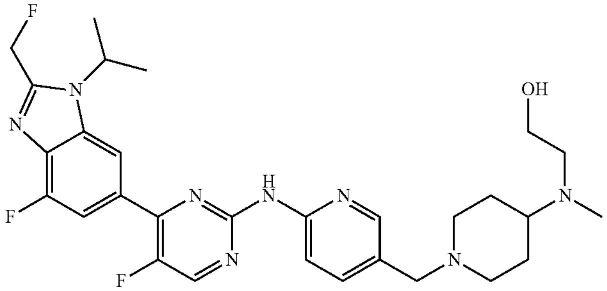 [SMILES: CC(C)n1c(CF)nc2c(F)cc(-c3nc(Nc4ccc(CN5CCC(N(C)CCO)CC5)cn4)ncc3F)cc21] | Reference to Example 3 | 570 |

-continued
| Compound ID | Compound structure | Synthesis method | M + 1 |
|---|---|---|---|
| 1990 | 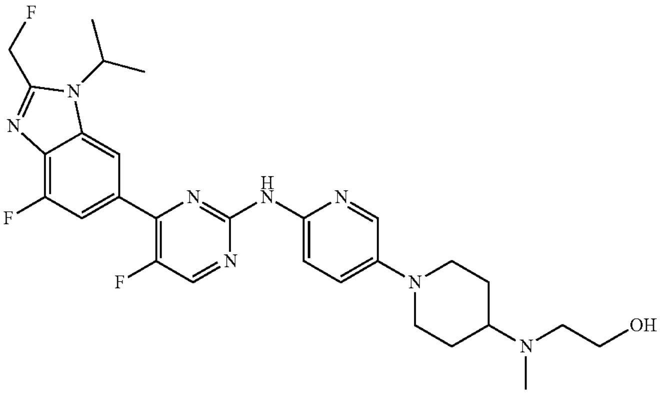 [SMILES: CC(C)n1c(CF)nc2c(F)cc(-c3nc(Nc4ccc(N5CCC(N(C)CCO)CC5)cn4)ncc3F)cc21] | Reference to Example 3 | 556 |
| 1987 | 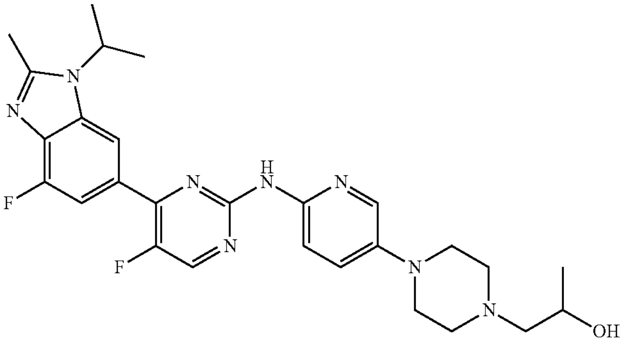 [SMILES: Cc1nc2c(F)cc(-c3nc(Nc4ccc(N5CCN(CC(C)O)CC5)cn4)ncc3F)cc2n1C(C)C] | Reference to Example 1 | 524 |
| 1983 | 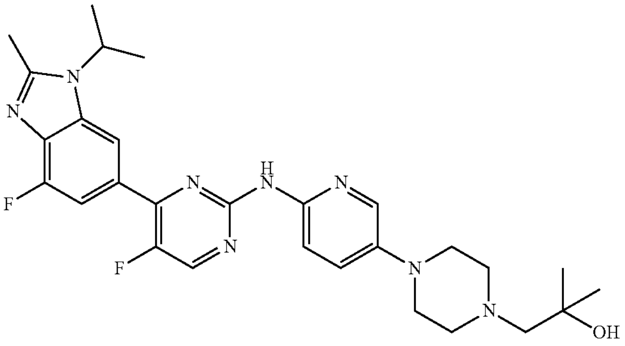 [SMILES: Cc1nc2c(F)cc(-c3nc(Nc4ccc(N5CCN(CC(C)(C)O)CC5)cn4)ncc3F)cc2n1C(C)C] | Reference to Example 1 | 552 |
| 1975 | 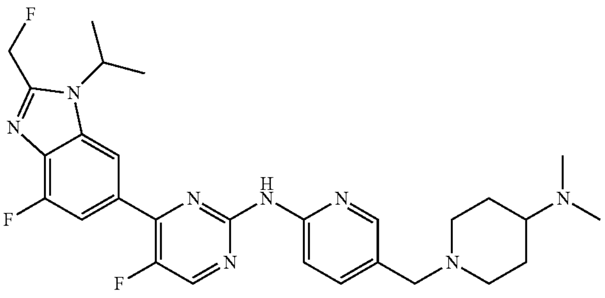 [SMILES: CC(C)n1c(CF)nc2c(F)cc(-c3nc(Nc4ccc(CN5CCC(N(C)C)CC5)cn4)ncc3F)cc21] | Reference to Example 3 | 540 |

-continued

| Compound ID | Compound structure | Synthesis method | M + 1 |
|---|---|---|---|
| 1964 | 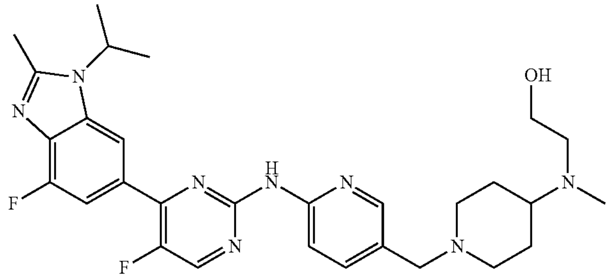 [SMILES: Cc1nc2c(F)cc(-c3nc(Nc4ccc(CN5CCC(N(C)CCO)CC5)cn4)ncc3F)cc2n1C(C)C] | Reference to Example 3 | 552 |

Example 5 Determination of Activity of CDK2 Kinase

The activity of CDK2 kinase in vitro was tested by the following method:

Final buffer:

100 mM 4-hydroxyethyl piperazine ethanesulfonic acid, pH 7.5;

0.1% bovine serum albumin;

0.01% Triton X-100;

1 mM dithiothreitol;

5 mM magnesium chloride;

10 μM sodium orthovanadate;

10 μM sodium P-glycerophosphate;

10 μM ATP;

1% DMSO (from the compound to be tested);

Substrate Peptide: 1 μM FAM-PKTPKKAKKL-OH, wherein FAM is 5-carboxyfluorescein;

0.1 nM CDK2/human cyclin E.

5 μL of buffer, 0.1 μL of compound to be tested (DMSO, 100 times the highest concentration) and 5 μL of substrate peptide buffer were added to a 384-well plate. The reaction was terminated with EDTA after culturing at 25° C. for 6 hours. Electrophoresis reading was started (Caliper LabChip® 3000 Drug Discovery System, blue laser (480 nm) for excitation, green CCD (520 nm) for detection of CCD2). The inhibitory effect of the compounds to be tested on the activity of CDK2 kinase was shown in Table 1.

Example 6 Determination of Activity of CDK4 Kinase

The activity of CDK4 kinase in vitro was tested by the following method:

Final buffer:

100 mM 4-hydroxyethyl piperazine ethanesulfonic acid, pH 7.5;

0.1% bovine serum albumin;

0.01% Triton X-100;

1 mM dithiothreitol;

5 mM magnesium chloride;

10 μM sodium orthovanadate;

10 μM sodium P-glycerophosphate;

25 μM ATP;

1% DMSO (from the compound to be tested);

Substrate Peptide: 1 μM FAM-RRFRPASPLRGPPK-$NH_2$ segment, wherein FAM is 5-carboxyfluorescein;

5 nM CDK4/human cyclin D1.

5 μL of buffer, 0.1 μL of compound to be tested (DMSO, 100 times the highest concentration) and 5 μL of substrate peptide buffer were added to a 384-well plate. The reaction was terminated with EDTA after culturing at 25° C. for 6 hours. Electrophoresis reading was started (Caliper LabChip® 3000 Drug Discovery System, blue laser (480 nm) for excitation, green CCD (520 nm) for detection of CCD2). The inhibitory effect of the compounds to be tested on the activity of CDK4 kinase was shown in Table 1.

Example 7 Determination of Activity of CDK6 Kinase

The activity of CDK6 kinase in vitro was tested by the following method:

2 nM CDK6/human cyclin D3 (Carna, No. 04-107)

Final buffer:

100 mM 4-hydroxyethyl piperazine ethanesulfonic acid, pH 7.5;

0.1% bovine serum albumin;

0.01% Triton X-100;

1 mM dithiothreitol;

5 mM magnesium chloride;

10 μM sodium orthovanadate;

10 μM sodium P-glycerophosphate;

300 μM ATP;

1% DMSO (from the compound to be tested);

Substrate peptide: Dyrktide;

5 μL of buffer, 0.1 μL of compound to be tested (DMSO, 100 times the highest concentration) and 5 μL of substrate peptide buffer were added to a 384-well plate. The reaction was terminated with EDTA after culturing at 25° C. for 3 hours. Electrophoresis reading was started (Caliper LabChip® 3000 Drug Discovery System, blue laser (480 nm) for excitation, green CCD (520 nm) for detection of CCD2). The inhibitory effect of the compounds to be tested on the activity of CDK6 kinase was shown in Table 1.

Example 8 Determination of Activity of MDA-MB-468 Cells

MDA-MB-468 (ATCC No. HTB-132);

RPMI 1640 (Invitrogen No. 22400089);

FBS (Hyclone No. SV30087.03);

Pen Strep (Hyclone No. SV30010);

CellTiter-Glo (Promega No. G7573);

Medium: 89% RPMI 1640, 10% FBS and 1% Pen Strep;

300 MDA-MB-468 cells and 50 μL of medium were inoculated in a plate with 100 μL of PBS buffer added, which was then cultured for 24 hours at 37° C./5% $CO_2$, then 250 nL of samples, which were taken from the compounds to be tested at ten test points and diluted with four times DMSO, were added to the plate wells and cultured for 5 days at 37° C./5% $CO_2$, then 25 μL of CellTiter-Glo was added to each plate well, followed by centrifugation by rotating (1000 rpm) for 15 seconds, and vibration mixing (400 rpm) for 10 minutes, the microplate reader Envision was started to read. The inhibitory effect of the compounds to be tested on the activity of MDA-MB-468 cells was shown in Table 1.

TABLE 1

IC50 data of the example compounds on activities of CDK2 kinase, CDK4 kinase, CDK6 kinase and MDA-MB-468 cells.

| Compound | CDK2/ CycE IC50 (nM) | CDK4/ CycD1 IC50 (nM) | CDK6/ CycD3 IC50 (nM) | MDA-MB-468 IC50 (nM) |
|---|---|---|---|---|
| 1963 | 101 | 1.78 | 1.0 | 459 |
| 1964 | 313 | 1.4 | 8.6 | 126 |
| 1967 | 122 | 0.17 | 1.23 | 682 |
| 1975 | 8.2 | 1.55 | 6.7 | 457 |
| 1978 | 459 | 2.6 | 9.8 | 1148 |
| 1979 | 163 | 0.83 | 4.1 | 1394 |
| 1983 | 489 | 1.9 | 4.5 | 986 |
| 1984 | 231 | 1.25 | 3.9 | 344 |
| 1985 | 128 | 0.98 | 3.0 | 454 |
| 1986 | 95 | 1.2 | 1.8 | 573 |
| 1987 | 355 | 1.2 | 5.9 | 345 |
| 1988 | 92 | 0.75 | 1.1 | 529 |
| 1990 | 5.3 | 1.54 | 4.8 | 276 |
| 1994 | 82 | 0.67 | 8.7 | 485 |
| 1995 | 6.2 | 1.75 | 10.1 | 186 |
| 1999 | 145 | 1.12 | 7.4 | 231 |
| Abemaciclib* | 504 | 1.96 | 9.9** | 1968 |

*Invest New Drugs (2014) 32, 825-837.

**refers to the CDK6/CycD1-inhibiting activity of Abemaciclib.

As seen from that, the pyrimidine derivative of the invention shows an excellent CDK-inhibiting effect and action, especially on CDK2, CDK4 and CDK6; and gives a lower IC50 value compared with Abemaciclib. In addition, when X includes a methoxy, hydroxyl or imine group, it shows a very excellent effect.

Finally, it should be noted that the above embodiments are only used to illustrate the technical solutions of the present invention and not to limit it; although the present invention has been described in detail with reference to the foregoing embodiments, it will be understood by one of ordinary skill in the art that the technical solutions described in the foregoing embodiments can still be modified or some technical features can be equivalently substituted; however, these modifications or substitutions do not make the essence of the corresponding technical solutions depart from the spirit and scope of the present invention.

INDUSTRIAL APPLICABILITY

The pyrimidine derivative provided in the invention shows an excellent CDK-inhibiting effect and action, especially on CDK2, CDK4 and CDK6; and shows a lower IC50 value compared with Abemaciclib; and can be used as an active ingredient for treating various diseases, such as abnormal cell proliferative diseases, infections, inflammatory diseases, autoimmune diseases, cardiovascular diseases or neurodegenerative diseases, hematopoietic toxic diseases caused by radiation, etc.

The invention claimed is:

1. A pyrimidine derivative, wherein the pyrimidine derivative is selected from a compound represented by Formula (I), or a tautomer, an enantiomer, a diastereomer, a mesomer, a racemate, or a mixture thereof, or a pharmaceutically acceptable salt or prodrug thereof:

Formula (I)

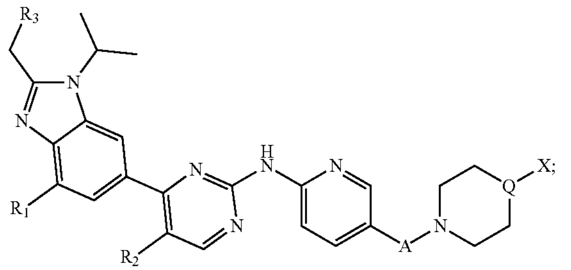

wherein $R_1$ and $R_2$ are fluorine;

$R_3$ is hydrogen;

A is a covalent bond;

Q is a carbon atom; X is —$NR_4R_6$, wherein $R_4$ is hydrogen;

$R_6$ is methyl.

2. A method for preparing the pyrimidine derivative according to claim 1, wherein the method comprises:

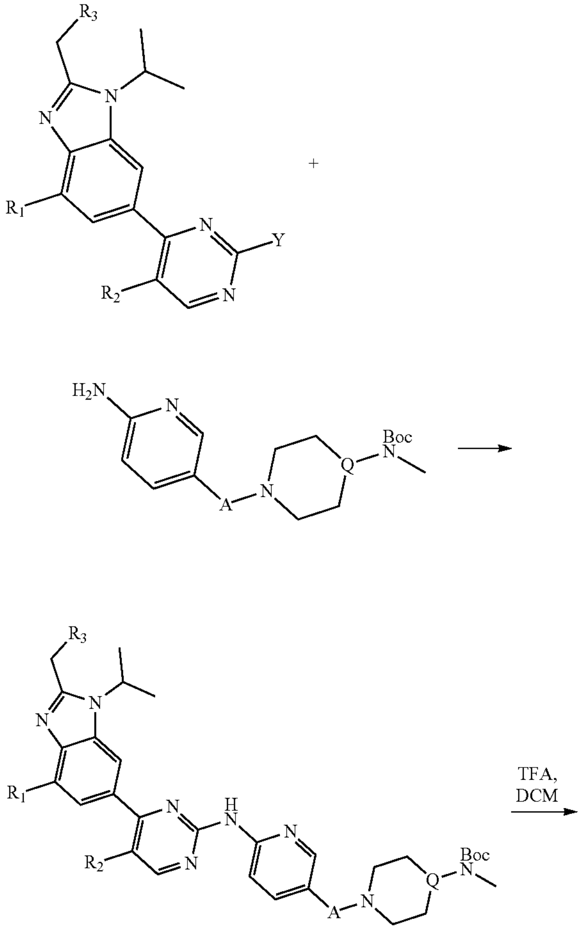

-continued

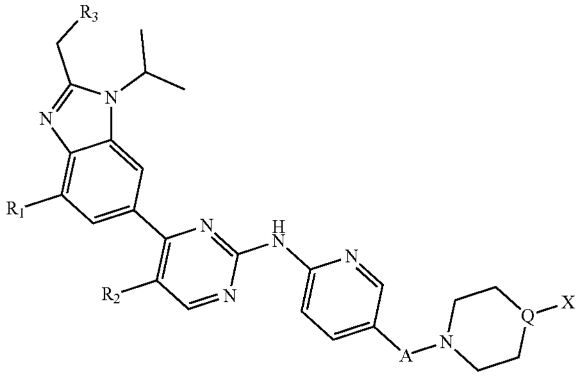

wherein, $R_1$, $R_2$, $R_3$, A, Q, and X have the same meanings as the corresponding groups in the pyrimidine derivative according to claim 1; Y is chlorine; Boc is tert-butoxycarbonyl that is an amino protecting group; TFA is trifluoroacetic acid; DCM is dichloromethane; and TFA and DCM are reagents for removing the Boc protecting group.

3. A method for treating abnormal cell proliferative diseases in a subject, comprising a step of administrating a therapeutically effective amount of the pyrimidine derivative according to claim 1 to the subject, wherein the abnormal cell proliferative disease is leukemia.

4. The method according to claim 3, wherein the leukemia is selected from acute myeloblastic leukemia, chronic myelocytic leukemia, acute lymphoblastic leukemia, or chronic lymphocytic leukemia.

5. A pharmaceutical composition, comprising the pyrimidine derivative according to claim 1 as an active ingredient and one or more pharmaceutically acceptable carriers, diluents, or excipients.

6. The pharmaceutical composition according to claim 5, further comprising one or more other anticancer agents as active ingredients, wherein the other anticancer agents are paclitaxel.

* * * * *